(12) United States Patent
Meetz et al.

(10) Patent No.: US 9,159,127 B2
(45) Date of Patent: Oct. 13, 2015

(54) DETECTING HAEMORRHAGIC STROKE IN CT IMAGE DATA

(75) Inventors: Kirsten Meetz, Eindhoven (NL); Thomas Buelow, Eindhoven (NL); Stewart Young, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1441 days.

(21) Appl. No.: 12/665,422

(22) PCT Filed: Jun. 17, 2008

(86) PCT No.: PCT/IB2008/052381
§ 371 (c)(1),
(2), (4) Date: Dec. 18, 2009

(87) PCT Pub. No.: WO2008/155718
PCT Pub. Date: Dec. 24, 2008

(65) Prior Publication Data
US 2010/0183211 A1   Jul. 22, 2010

(30) Foreign Application Priority Data

Jun. 20, 2007   (EP) .................................... 07110672

(51) Int. Cl.
*G06T 7/00* (2006.01)
*A61B 6/00* (2006.01)
*G06T 7/40* (2006.01)

(52) U.S. Cl.
CPC .............. *G06T 7/0012* (2013.01); *A61B 6/501* (2013.01); *A61B 2576/026* (2013.01);
(Continued)

(58) Field of Classification Search
CPC ............ A61B 6/03; G06T 2207/20144; G06T 2207/30016; G06T 7/0081
USPC ........................................................ 382/131
See application file for complete search history.

(56) References Cited

U.S. PATENT DOCUMENTS

| 6,235,489 B1 | 5/2001 | Jackowski |
| 6,792,302 B2 | 9/2004 | Wintermark et al. |

(Continued)

FOREIGN PATENT DOCUMENTS

| EP | 1521083 A2 | 4/2005 |
| JP | 2007-044485 A | 2/2007 |
| WO | 02069799 A1 | 9/2002 |

OTHER PUBLICATIONS

Chan ("Computer aided detection of small acute intracranial hemorrhage on computer tomography of brain", published online Mar. 21, 2007, Computerized Medical Imaging and Graphics, vol. 31, pp. 285-298.*

(Continued)

*Primary Examiner* — David J Makiya
*Assistant Examiner* — John Corbett

(57) ABSTRACT

The invention relates to a system (100) arranged to delineate the acute intracerebral haematoma in non-contrasted CT images in two stages. The first stage, performed by the extraction unit (110), employs an analysis of gray values of the image data in order to extract the candidate region. The candidate region may comprise both an acute haematoma and other regions having similar gray values, e.g., regions resulting from partial volume effects at the interface of the bony structures of the skull and the brain. The novel second stage, performed by the classification unit (120), analyzes spatial features of the candidate region such as, for example, the size, shape, and connectedness to the skull bone of the candidate region. Using spatial features of the candidate region improves the correctness of classification of the candidate region as a true or false acute haematoma.

17 Claims, 6 Drawing Sheets

(52) U.S. Cl.
CPC ...... *G06T 7/403* (2013.01); *G06T 2207/10081* (2013.01); *G06T 2207/20148* (2013.01); *G06T 2207/20156* (2013.01); *G06T 2207/30016* (2013.01); *G06T 2210/41* (2013.01)

(56) References Cited

U.S. PATENT DOCUMENTS

| | | | |
|---|---|---|---|
| 7,037,267 | B1 | 5/2006 | Lipson et al. |
| 2006/0142983 | A1 | 6/2006 | Sorensen et al. |
| 2007/0031020 | A1* | 2/2007 | Li .............................. 382/131 |
| 2010/0049035 | A1* | 2/2010 | Hu et al. ..................... 600/425 |

OTHER PUBLICATIONS

Liao et al., Automatic Detection of Intracranial Hematoma on Routine Brain CT, 2005, The Journal of Taiwan Association for Medical Informatics, vol. 14, Issue 4, pp. 77-94.*

PTO 14-0010 by Schreiber Translations, Oct. 2013, 34 pages For English translation for Liao et al., "Automatic Detection of Intracranial Hematoma on Routine Brain CT", 2005, The Journal of Taiwan Association for Medical Informatics, vol. 14, Issue 4, pp. 77-94.*

Gonzalez et al., "Digital Image Processing", 1992, Addison-Wesley Publishing Company, Inc., ISBN 0-201-60078-1.*

Meetz et al., "Automated detection of acute haemorrhagic stroke in non-contrasted CT images", Jun. 29, 2007, International Journal of Computer Assisted Radiology and Surgery, Special Session on Abdomen and Brain, vol. 2, Issue 1, Supplement, pp. S373-S397.*

Brummer et al., Automatic Detection of Brain Contours in MRI Data Sets, 1991, Lecture Notes in Computer Science, vol. 511, pp. 188-204.*

Oikarinen, Using 2- and 2 1/2- Dimensional Seed Filling in View Lattice to Accelerate Volumetric Rendering, 1998, Computers and Graphics, vol. 22, No. 6, pp. 745-757.*

Xiao et al., Automatic Diagnosis of Intracranial Hematoma on Brain CT Using Knowledge Discovery Techniques: Is Finer Resolution Better?, Aug. 26, 2008, Biomedical Engineering: Applications, Basis and Communications, vol. 20, No. 6, pp. 401-408.*

Castellanos, M., et al.; Predictors of good outcome in medium to large spontaneous supratentorial intracerebral haemorrhages; 2005; J. of Neurology, Neurosurgery and Psychiatry; 76(5)691-695.

Chin, D., et al.; Acute Cerebellar Hemorrhage with Brainstem Compression in Contrast with Benign Cerebellar Hemorrhage; 1983; Surgical Neurology; 19(5)406-409.

Dhawan, A. P., et al.; Image analysis and 3-D visualization of intracerebral brainhemorrhage; 1993; IEEE Trans on Computer-Based Medical Systems; abstract.

Konig, M., et al.; Diagnosis of Cerebral Infarction Using Perfusion CT: State of the Art; 2000; Electromedica; 68:9-13.

Matesin, M., et al.; A Rule-Based Approach to Stroke Lesion Analysis from CT Brain Images; 2001; Image and Signal Processing and Analysis; pp. 219-223.

Meetz, K. "Automated Detection of Acute Haemorrhagic Stroke in Non-Contrasted CT Images". Philips Research, Dept. Technical System, Hamburg, Germany (2003).

Baumgartner, C. et al. "Functional cluster analysis of CT perfusion maps: A new tool for diagnosis of acute stroke", Journal of Digital Imaging, Col. 1 8, No. 3 (Sep.), 2005: pp. 219-226.

* cited by examiner

DETECTING HAEMORRHAGIC STROKE IN CT IMAGE DATA

FIELD OF THE INVENTION

The invention relates to the field of assisting physicians in medical diagnosing and more specifically in detecting haemorrhagic stroke in CT image data.

BACKGROUND OF THE INVENTION

Stroke is the third leading cause of death in the US and western countries after myocardial infarct and cancer, and the leading cause of disability. Besides the dramatic decrease of the individuals' quality of life, stroke has an evident socio-economic impact with costs of 35 to 50 thousand US $ per stroke survivor per year.

Concerning these facts, there is a strong need for an effective treatment of stroke patients. During the last decade, studies of recanalizing drugs and neuroprotectants in acute ischemic stroke patients have shown promising results. However, this treatment has to be applied within a narrow window of time following the stroke. After six hours the relative risk of the therapy outweighs its benefits. Although the treatment is helpful when applied to patients with acute ischemic stroke, it is hazardous when applied to patients with an acute cerebral bleeding, e.g., haemorrhagic stroke, or event with a disposition for cerebral bleeding.

Both time-pressure and the hazardous effect on patients with cerebral bleeding demand a fast, qualified, differential diagnosis of the stroke based on adequate imaging and image reading techniques. However, these techniques are available to very few medical specialists, hence currently only 3-4% of patients with acute ischemic stroke are treated with an adequate therapy like intravenous thrombolysis.

In CT imaging, an acute haemorrhagic stroke can be characterized by typical gray value characteristics that change in the course of the disease. In an acute phase the stroke region is depicted as a hyperdense, i.e., relatively brighter area, whereas a chronic haemorrhagic stroke appears as a hypodense, i.e., relatively darker area. These typical gray values demand for image processing approaches like thresholding, clustering and region growing.

In the article entitled "Image Analysis and 3-D Visualization of Intracerebral Brain Hemorrhage ", Dhawan et al, proceedings of Sixth Annual IEEE Symposium on Computer-Based Medical Systems (13-16 Jun. 1993). pages 140 -145 , Dhawan et al propose a semi-automatic approach to detect intracerebral haemorrhage based on CT images, A k-means clustering algorithm subdivides the entire image into foreground and background. On the resulting binary image , the user selects an adequate seed point for a subsequent region growing algorithm that delineates the intracerebral haemorrhage.

A more automated rule-based approach is presented by M. Matesin et al. in the article entitled "A rule-based approach to stroke lesion analysis from CT images", in Image and Signal Processing and Analysis, 2001, pages 219-223. Here image features like brightness and symmetry, relative to the symmetry axis of the brain, of an extracted region are used to classify the image into background, skull, cerebrospinal fluid, gray/white matter and stroke. An area of stroke that is not symmetric with respect to the symmetry axis of the brain is labeled as hypodense by the authors. These assumptions may be true for an ischemic stroke, but do not correctly describe an acute haematoma.

SUMMARY OF THE INVENTION

It would be advantageous to have a system capable of assisting a physician in making the differential diagnosis of stroke patients, based on non-contrasted CT images.

To better address this issue, in an aspect of the invention, a system for identifying an acute haematoma in non-contrasted CT image data is provided, the system comprising:
an extraction unit for extracting a candidate region suspected to be the acute haematoma, based on a first analysis of gray values of the image data; and
a classification unit for classifying the candidate region as a positive or negative acute haematoma, based on a second analysis of spatial features of the candidate region.

The system is thus arranged to delineate the acute intracerebral haematoma in non-contrasted CT images in two stages. The first stage, performed by the extraction unit, relies on the first analysis of gray values of the image data in order to extract the candidate region. The candidate region may comprise both an acute haematoma and other regions having similar gray values, e.g., regions resulting from partial volume effects at the interface of the bony structures of the skull and the brain. The novel second stage, performed by the classification unit, relies on the second analysis of spatial features of the candidate region such as, for example, the size, shape, and connectedness to the skull bone of the candidate region. Using spatial features of the candidate region improves the correctness of the classification of the candidate region as a true or false acute haematoma. Thus, the system is useful in more reliably classifying the candidate region extracted by the extraction unit. This helps both a stroke expert and, in particular, a non-stroke-expert in reaching a correct diagnosis and prescribing an effective therapy. Further, the system does not require CT image data obtained using contrast agents.

In an embodiment of the system, the extraction unit comprises:
a skull unit for extracting a skull region;
a brain unit for extracting a brain region, based on the extracted skull region; and
a haematoma unit for extracting the candidate region within the brain region.

Extracting the skull region can be easily carried out on the basis of the gray values of the skull bone. Extraction of the brain region may be easily carried out on the basis of the gray values of the brain tissue within an area bounded by the skull. Extracting the candidate region within the brain region may be easily carried out on the basis of the gray values of the acute haematoma.

In an embodiment of the system, the classification unit comprises:
a topology unit for computing a topological feature of the candidate region; and/or
a geometry unit for computing a geometrical feature of the candidate region; and
a discrimination unit for classifying the candidate region on the basis of the topological and/or geometrical feature of the candidate region.

Based on the computed topological and/or geometrical feature of the skull of the candidate region, the discrimination unit may better classify the candidate region as an acute haematoma. Optionally, the computed topological and/or geometrical feature may be used by the discrimination unit to identify an acute intracranial haematoma, acute subdural haematoma, acute epidural haematoma, or partial volume effect.

In an embodiment of the system, the topological and/or geometrical feature of the candidate region is computed based on a distance-based histogram of the mean gray value of the candidate region. First, the Euclidean distance map of the brain is calculated. Second, a distance-based histogram comprising mean gray values at discrete distance intervals is calculated using the distance map. The distance histogram provides a simple way of visualizing and determining the type of the candidate region.

It will be appreciated by those skilled in the art that any two or more of the above-mentioned embodiments of the system may be combined in any useful way.

In a further aspect of the invention, the system according to the invention is comprised in an image acquisition apparatus.

In a further aspect of the invention, the system according to the invention is comprised in a workstation.

In a further aspect of the invention, a method of identifying an acute haematoma in non-contrasted CT image data is provided, the method comprising:

an extraction step for extracting a candidate region suspected to be the acute haematoma, based on a first analysis of gray values of the image data; and a classification step for classifying the candidate region as a positive or negative acute haematoma, based on a second analysis of spatial features of the candidate region.

In a further aspect of the invention, a computer program product to be loaded by a computer arrangement is provided, the computer program product comprising instructions for identifying an acute haematoma in non-contrasted CT image data, the computer arrangement comprising a processing unit and a memory, the computer program product, after being loaded, providing said processing unit with the capability to carry out the following tasks:

extracting a candidate region suspected to be the acute haematoma, based on a first analysis of gray values of the image data; and classifying the candidate region as a positive or negative acute haematoma, based on a second analysis of spatial features of the candidate region.

Modifications and variations of the image acquisition apparatus, of the workstation, of the method, and/or of the computer program product which correspond to the described modifications and variations of the system, can be carried out by a skilled person on the basis of the present description.

BRIEF DESCRIPTION OF THE DRAWINGS

These and other aspects of the invention will become apparent from and will be elucidated with respect to the implementations and embodiments described hereinafter and with reference to the accompanying drawings, wherein.

Identical reference numerals are used to denote similar parts throughout the Figures.

DETAILED DESCRIPTION OF EMBODIMENTS

Figure 1:
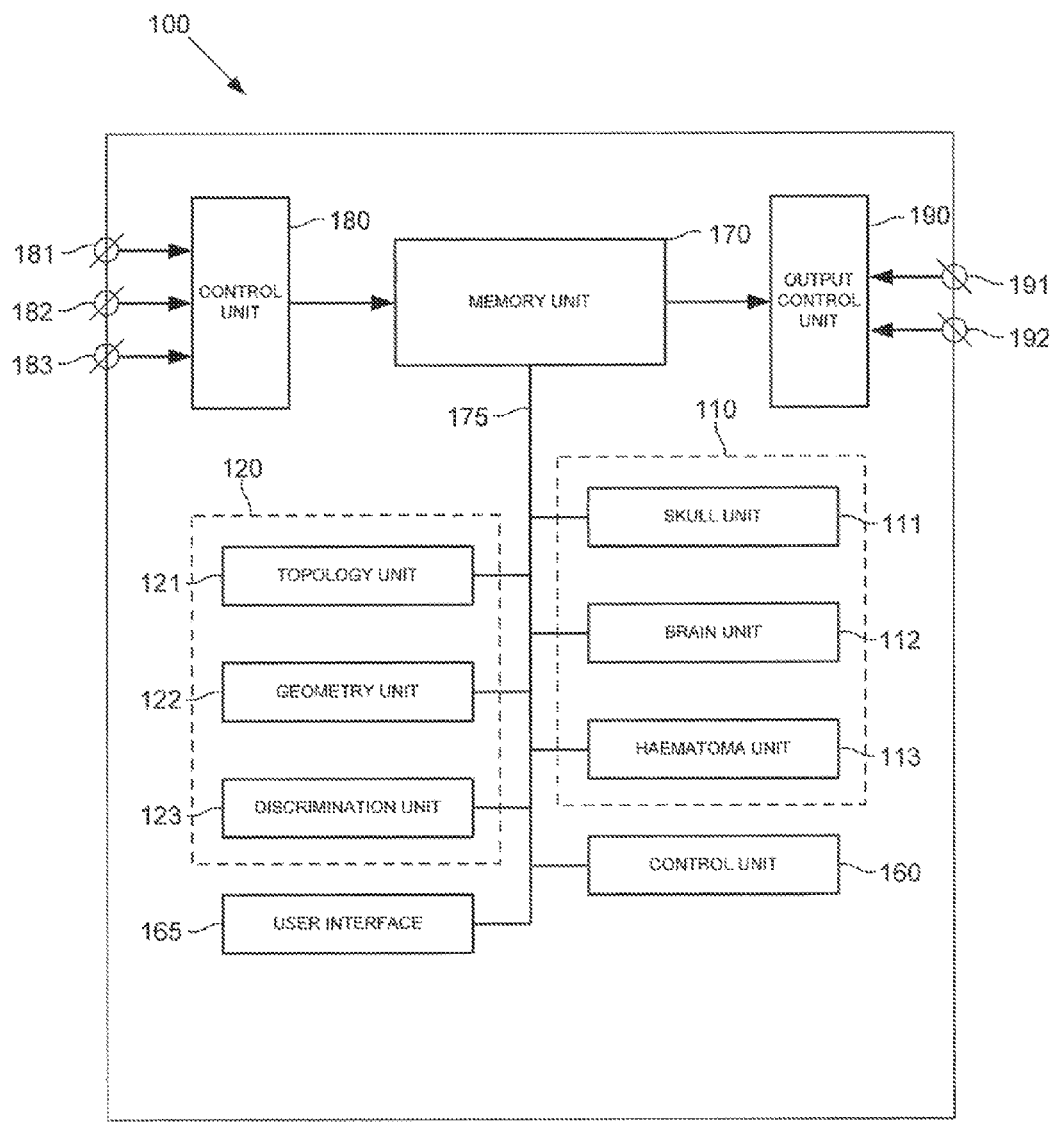
FIG. 1 schematically shows a block diagram of an exemplary embodiment of the system.

FIG. 1 schematically shows a block diagram of an exemplary embodiment of the system 100 for identifying an acute haematoma in non-contrasted CT image data, the system comprising:

an extraction unit 110 for extracting a candidate region suspected to be the acute haematoma, based on a first analysis of gray values of the image data; and a classification unit 120 for classifying the candidate region as a positive or negative acute haematoma, based on a second analysis of spatial features of the candidate region.

The exemplary embodiment of the system 100 further comprises the following units:

a skull unit 111 for extracting a skull region;

a brain unit 112 for extracting a brain region, based on the extracted skull region; and a haematoma unit 113 for extracting the candidate region within the brain region;

a topology unit 121 for computing a topological feature of the candidate region;

a geometry unit 122 for computing a geometrical feature of the candidate region; and a discrimination unit 123 for classifying the candidate region on the basis of the topological feature and the geometrical feature of the candidate region;

a user interface 165 for communicating with a user of the system 100; and a memory unit 170 for storing data.

In an embodiment of the system 100, there are three input connectors 181, 182 and 183 for the incoming data. The first input connector 181 is arranged to receive data coming in from a data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to a data storage means such as a hard disk, a magnetic tape, a flash memory, or an optical disk. The second output connector 192 is arranged to output the data to a display device. The output connectors 191 and 192 receive the respective data via an output control unit 190.

The skilled person will understand that there are many ways to connect input devices to the input connectors 181, 182 and 183 and the output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analogue telephone network.

In an embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data may comprise, for example, the image data. The memory unit 170 may be implemented by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, the CT image data comprising a delineation of the candidate region classified as a true acute haematoma. The memory unit 170 may be also arranged to receive data from and deliver data to the units of the system 100 comprising the extraction unit 110, the classification unit 120, the skull unit 111, the brain unit 112, the haematoma unit 113, the topology unit 121, the geometry unit 122, the discrimination unit 123, the control unit 160, and the user interface 165, via a memory bus 175. The memory unit 170 is further arranged to make the output data available to external devices via any of the output connectors 191 and 192. Storing data from the units of the system 100 in the memory unit 170 may advantageously improve performance of the units of the system 100 as well as the rate of transfer of the output data from the units of the system 100 to external devices.

Alternatively, the system 100 may comprise no memory unit 170 and no memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In an embodiment of the system 100, the system 100 comprises a control unit 160 for controlling the workflow in the system 100. The control unit may be arranged to receive control data from and provide control data to the units of the system 100. For example, after the candidate region is extracted by the extraction unit 110, the extraction unit 110 may be arranged to pass a control data "the candidate region is extracted" to the control unit 160 and the control unit 160 may be arranged to provide a control data "classify the candidate region" to the classification unit 120, thereby requesting the classification unit 120 to classify the candidate region. Alternatively, a control function may be implemented in another unit of the system 100.

In an embodiment of the system 100, the system 100 comprises a user interface 165 for communicating with the user of the system 100. The user interface 165 may be arranged to obtain a user input, e.g., an input to request displaying a view computed from the image data or a threshold value in Hounsfield units (HU) for extracting the skull. The skilled person will understand that more functions may be advantageously implemented in the user interface 165 of the system 100.

Figure 2:
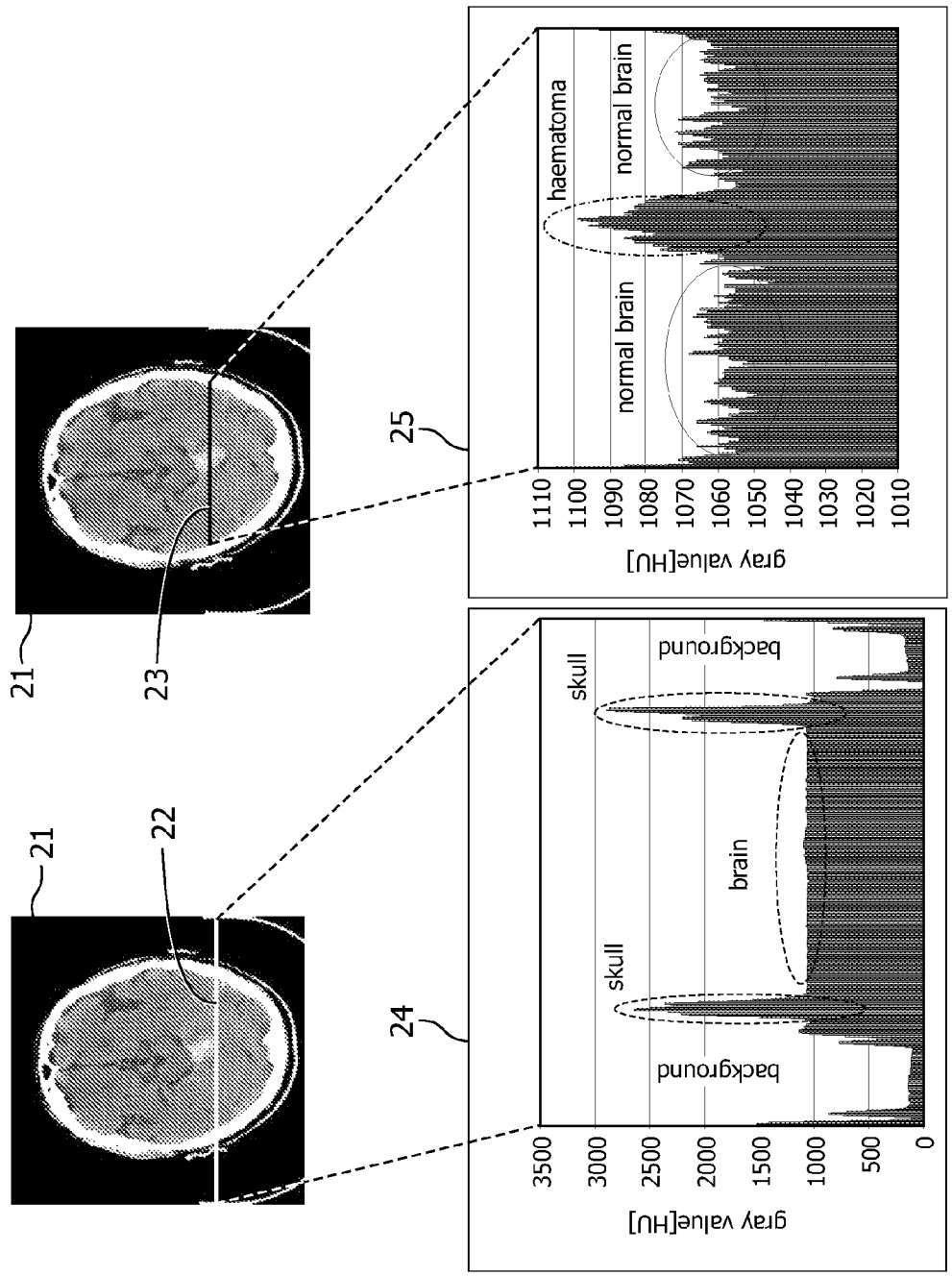
FIG. 2 shows gray value profiles of the head and the brain.

FIG. 2 shows gray value profiles of the head and the brain. The left profile 24 is the head profile and corresponds to voxels aligned along an interval 22 in a slice 21 of the CT image data. This profile allows identifying three regions: the skull region corresponding to gray values greater than a skull threshold $T_{skull}$ of 1133 HU, the brain region corresponding to gray values less than the skull threshold $T_{skull}$ and greater than a brain threshold $T_{brain}$ of 500 HU, and the background region corresponding to gray values less than the brain threshold $T_{brain}$. The right profile 25 is the brain profile and corresponds to voxels aligned along an interval 23 in the slice 21 of the CT image data. This profile allows identifying two tissue classes within the brain: normal brain tissue corresponding to gray values lower than a haematoma threshold $T_{haematoma}$ of 1080 HU and a candidate region corresponding to gray values greater than the haematoma threshold $T_{haematoma}$. To make the determined regions spatially consistent, a region growing approach may be used. Further, the image data may be preprocessed and/or postprocessed using various filtering operators, e.g., morphology operators.

The skilled person will understand that the thresholds may be determined experimentally, based on an expert evaluation of a set of training images. The actual thresholds will depend on said set of training images and the expert evaluation and may be different from the values described in the preceding paragraph. More regions, and thresholds describing these regions, corresponding to, e.g., tumors, motion artifacts, and calcifications, may be defined and identified in a similar way.

The extraction unit 110 is arranged for extracting a candidate region suspected to be the acute haematoma, based on a first analysis of gray values of the image data. The first analysis may involve using region growing and thresholding. A connected component of a seed, the component comprising voxels with gray values between the haematoma threshold $T_{haematoma}$ and the skull threshold $T_{skull}$, is extracted as the candidate region.

An acute intracerebral haematoma has to be within the brain, which is surrounded by the skull. This fact may be used to improve the extraction strategy. In an embodiment of the system 100, the extraction unit comprises a skull unit 111 for extracting a skull region, a brain unit 112 for extracting a brain region, based on the extracted skull region, and a haematoma unit 113 for extracting the candidate region within the brain region. First, a region growing approach is applied to extract the skull region. Assuming that there will be no other object surrounding the skull that provides similar gray values, the seed is automatically extracted by casting rays from the border of the image volume. If a ray hits an object within the given gray value range, e.g., greater than $T_{skull}$, and with an extension greater than 3 mm, a seed is set within this object. The skull unit determines the binary mask of the skull defining the skull region.

After the skull unit 111 has extracted the skull region, the brain unit 112 is arranged to use the region growing approach to extract the brain region. Here the seed may be a center of the skull region, e.g., the mass center or the geometrical center. The connected component of the seed, the component comprising voxels with gray values between the brain threshold $T_{brain}$ and the skull threshold $T_{skull}$, is extracted as the brain region.

After the brain unit 112 has extracted the brain region, the haematoma unit 113 is arranged to extract a set of candidate regions within the brain region. This is achieved by identifying voxels within the brain region with gray values greater than the haematoma threshold $T_{haematoma}$. The set of connectivity components of the identified voxels is the set of candidate regions.

Unfortunately, partial volume effects at the interface of the bony structures and the brain provide similar gray values as acute haematoma. Thus, the set of candidate regions may include a considerable amount of false positives induced by partial volume effects. In particular, acute subdural and epidural haematoma, which reside at the skull-brain interface, are hard to discriminate from partial volume effects.

The classification unit 120 is arranged to classify the candidate region as a positive or negative acute haematoma, based on a second analysis of spatial features of the candidate region. In an embodiment, the main discriminating criterion is the simultaneous occurrence of the topological feature "connected to bone" and the geometrical feature "extension perpendicular to the skull's surface". The topology unit 121 is arranged to compute the distance between the candidate region and the skull. The geometry unit 122 is arranged to compute the dimensions of the candidate region. The discrimination unit 123 is arranged to classify the candidate region, based on the connectedness and dimensions of the candidate region. If the distance between the candidate region and the skull is less than a distance threshold, the candidate region is adjacent to the skull. If the extension perpendicular to the skull's surface of such a candidate region is greater than a dimension threshold, the candidate region is classified as an acute subdural or epidural haematoma. Otherwise, such a candidate region is classified as a partial volume artifact. If the candidate region is not adjacent to the skull, i.e., if the distance between the candidate region and the skull is greater than or equal to the distance threshold, then the candidate region is classified as an acute intracranial haematoma.

Alternatively, in an embodiment, the classification unit 120 is arranged to compute and analyze a distance-based histogram. First, the Euclidean distance map of the brain is calculated. The Euclidean distance map of the brain assigns, to each point of a plurality of points of the brain, the Euclidean distance from the point to the skull. The points of the plurality of points of the brain are binned, based on their distance from the skull. The bin intervals may be, for example, 1 mm in length. For each candidate region and each bin, the mean of gray values of points is computed. This results in a typical distance-based histogram comprising peaks with nearly the same mean gray value for each bin interval, approximately 1100 HU, but with different peak distribution patterns.

Figure 3:
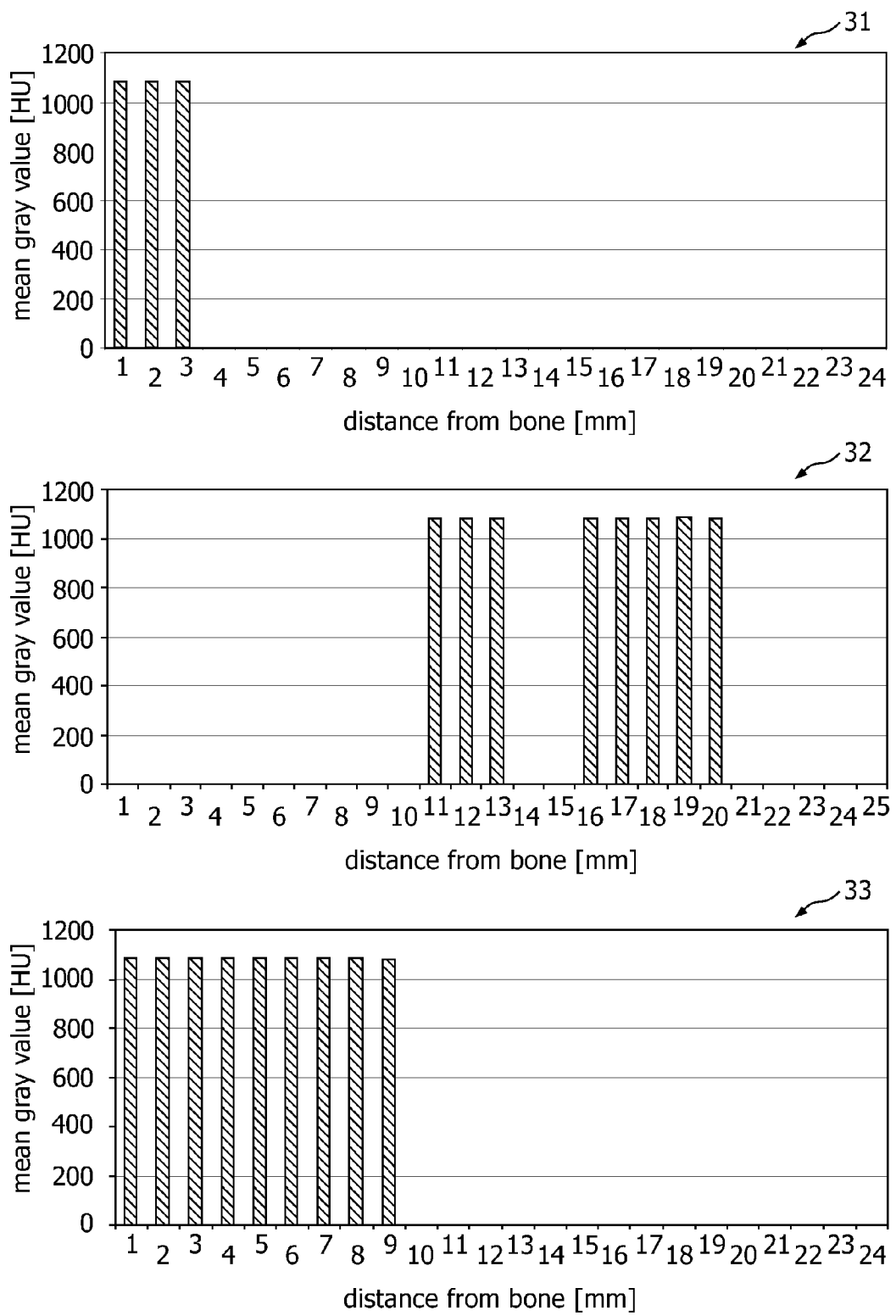
FIG. 3 shows exemplary distance-based histograms.

FIG. 3 shows exemplary distance-based histograms. Partial volume effects are described by narrow peaks, which are directly connected to bony structures, as shown in the diagram 31. Candidate regions defining peaks starting at a distance of 0 mm and ending at a distance of 4 mm or less than 4 mm are classified as partial volume artifacts, i.e. negative acute haematoma. A positive acute haematoma has either no connection to any bone, as shown in the diagram 32, or, if connected to the skull, shows a relatively broader peak, illustrated in the diagram 33.

The skilled person will understand that various methods and numerous topological and/or geometrical features may be useful for classifying the candidate region. The described methods and features are used to illustrate the invention and must not be construed as limiting the scope of the claims.

The skilled person will further understand that the system may be arranged to extract and classify candidate regions on the basis of multidimensional data, e.g. two-dimensional or three-dimensional image data.

The skilled person will further understand that the system 100 described in the current document may be a valuable tool for assisting a physician in medical diagnosing, in particular in extracting information from and interpreting medical image data.

The skilled person will further understand that other embodiments of the system 100 are also possible. It is possible, among other things, to redefine the units of the system and to redistribute their functions.

The units of the system 100 may be implemented using a processor. Normally, their functions are performed under the control of a software program product. During execution, the software program product is normally loaded into a memory, like a RAM, and executed from there. The program may be loaded from a background memory, such as a ROM, hard disk, or magnetic and/or optical storage, or may be loaded via a network like the Internet. Optionally, an application-specific integrated circuit may provide the described functionality.

Figure 4:
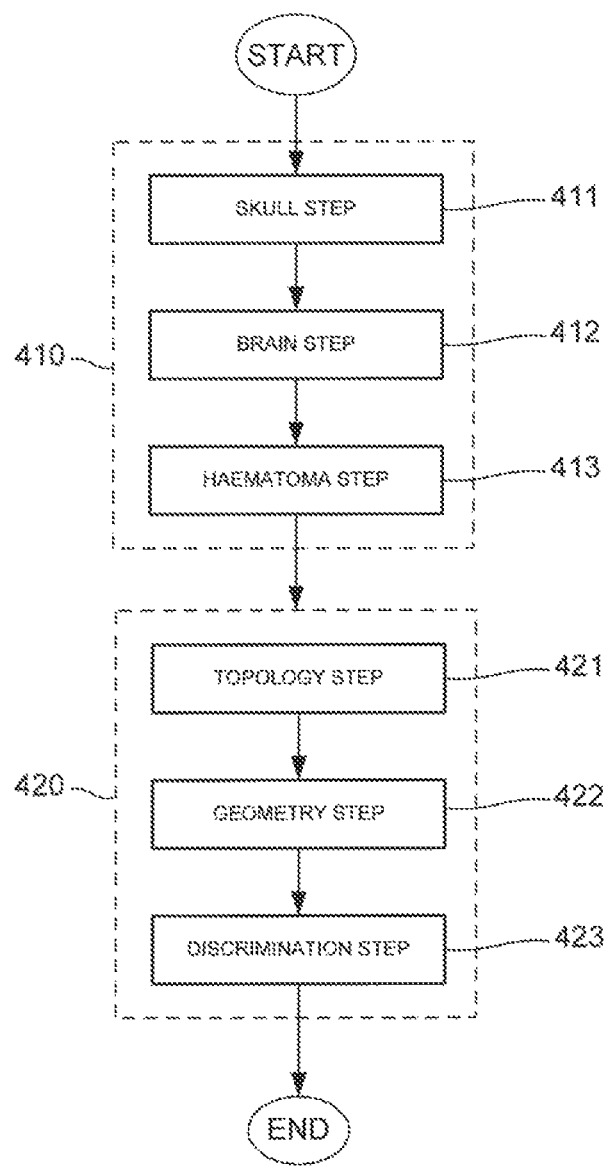
FIG. 4 shows a flowchart of an exemplary implementation of the method.

FIG. 4 shows a flowchart of an exemplary implementation of the method 400 of identifying an acute haematoma in non-contrasted CT image data. The method 400 begins with an extraction step 410 for extracting a candidate region suspected to be the acute haematoma, based on a first analysis of gray values of the image data. After the extraction step 410, the method 400 continues to a classification step 420 for classifying the candidate region as a positive or negative acute haematoma, based on a second analysis of spatial features of the candidate region. After the classification step, the method 400 terminates.

In an embodiment shown, the extraction step 410 compresses the following steps: a skull step 411, a brain step 412, and a haematoma step 413. The extraction step 410 begins with the skull step 411 for extracting a skull region. After the skull step, the extraction step 410 continues to the brain step 412 for extracting a brain region, based on the extracted skull region. After the brain step 412, the extraction step 410 continues to the haematoma step 413 for extracting the candidate region within the brain region.

In an embodiment shown, the classification step 420 comprises a topology step 421, a geometry step 422, and a discrimination step 423. The classification step 420 begins with the topology step 421 for computing a topological feature of the candidate region. After the topology step 421, the classification step 420 continues to the geometry step 422 for computing a geometrical feature of the candidate region. After the geometry step 422, the classification step 420 continues to the discrimination step 423 for classifying the candidate region on the basis of the topological feature and the geometrical feature of the candidate region.

The order of steps in the method 400 is not mandatory, the skilled person may change the order of some steps or perform some steps concurrently using threading models, multi-processor systems or multiple processes without departing from the concept as intended by the present invention. Optionally, two or more steps of the method 400 of the current invention may be combined into one step. Optionally, a step of the method 400 of the current invention may be split into a plurality of steps.

Figure 5:
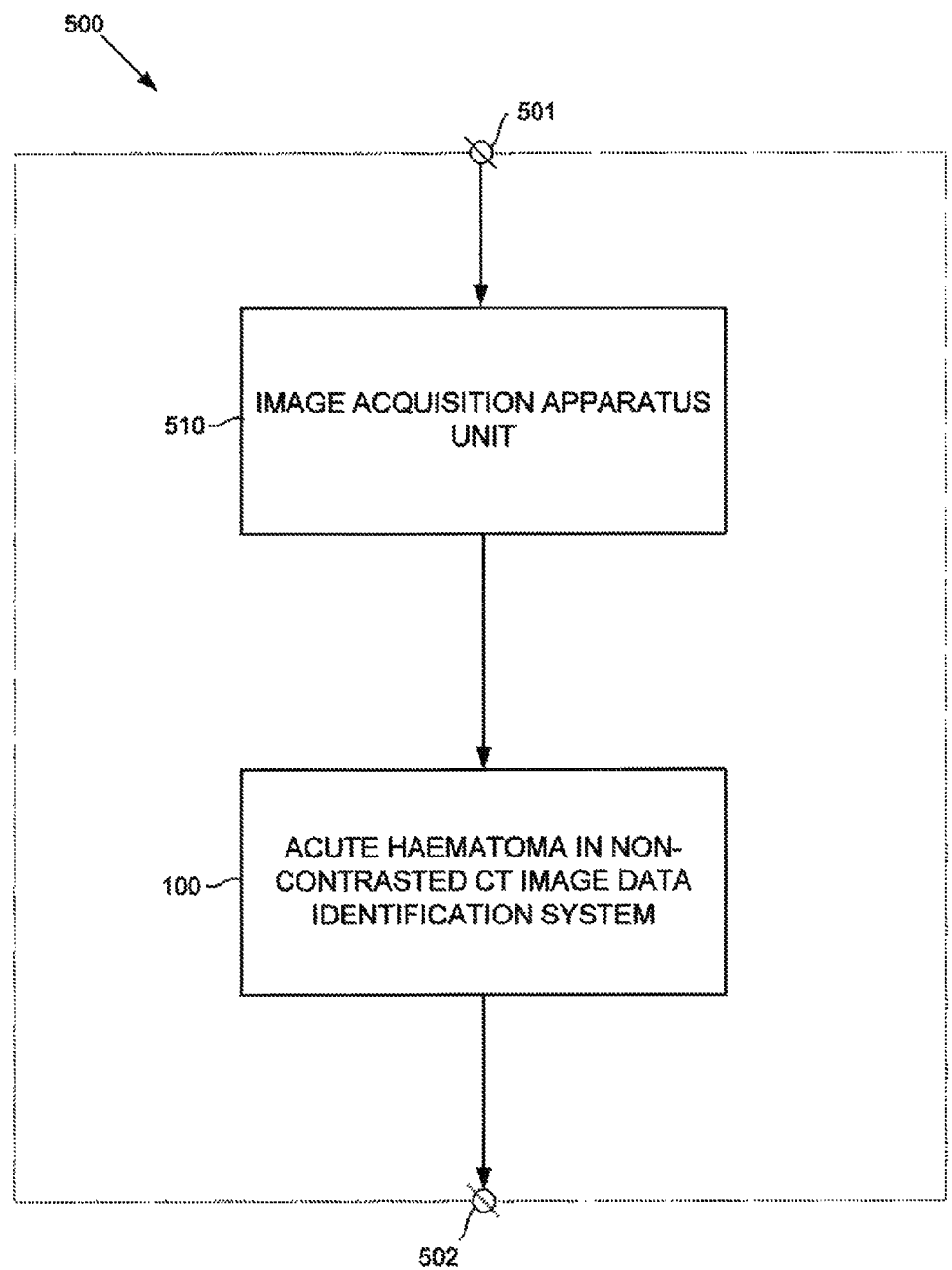
FIG. 5 schematically shows an exemplary embodiment of the image acquisition apparatus.

FIG. 5 schematically shows an exemplary embodiment of the image acquisition apparatus 500 employing the system 100, said image acquisition apparatus 500 comprising a CT image acquisition unit 510 connected, via an internal connection, with the system 100, an input connector 501, and an output connector 502. This arrangement advantageously increases the capabilities of the image acquisition apparatus 500, providing said image acquisition apparatus 500 with advantageous capabilities of the system 100.

Figure 6:
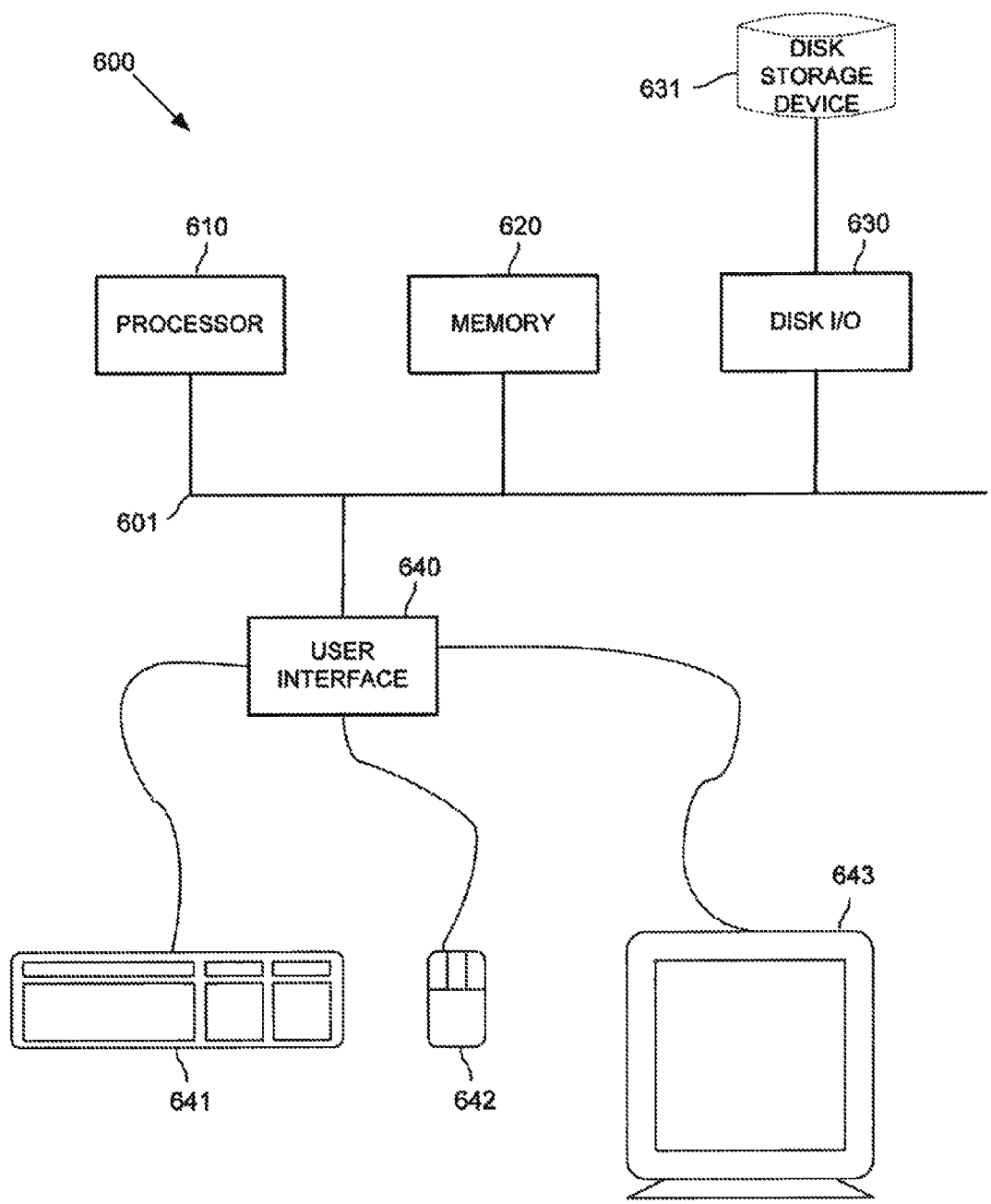
FIG. 6 schematically shows an exemplary embodiment of the workstation.

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 60 of the invention, implemented as a computer program, is stored in the disk storage device 631. The workstation 600 is arranged to load the program and input data into memory 620 and execute the program on the processor 610. The user can input information to the workstation 600, using the keyboard 641 and/or the mouse 642. The workstation is arranged to output information to the display device 643 and/or to the disk 631. The skilled person will understand that numerous other embodiments of the workstation 600 are known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, etc., does not indicate any ordering. These words are to be interpreted as names.

The invention claimed is:

1. A system for identifying an acute haematoma in non-contrasted computed tomography image data, the system comprising a computer programmed to:
   perform a first analysis of gray values of non-contrasted computer tomography image data, the first analysis comprising region growing and thresholding;
   extract a candidate region suspected to be the acute haematoma, based on the first analysis of the gray values;
   perform a second analysis of spatial features of the candidate region, including a size of the candidate region, a shape of the candidate region, and a connectedness of the candidate region to a skull; and
   classify, via a distance-based histogram of a mean gray value of the candidate region, the candidate region as a positive or negative acute haematoma, based on the analysis of spatial features.

2. The system as claimed in claim 1, wherein extracting the candidate region comprises:
   extracting a skull region;
   extracting a brain region, based on the extracted skull region; and
   extracting the candidate region from within the brain region.

3. The system as claimed in claim 1, wherein classifying the candidate region comprises:
   computing a topological feature of the candidate region; and/or
   computing a geometrical feature of the candidate region; and
   classifying the candidate region on the basis of the topological and/or geometrical feature of the candidate region.

4. The system as claimed in claim 3, wherein the topological and/or geometrical feature of the candidate region is computed, based on the distance-based histogram of the mean gray value of the candidate region.

5. The system as claimed in claim 4, wherein the computer is programmed to:
   compute the topology feature by computing connectedness of the candidate region to the skull in accordance with a distance between the candidate region and the skull;
   compute the geometry feature by computing dimensions of the candidate region; and
   classify the candidate region by classifying the candidate region in accordance with the computed connectedness and the dimensions of the candidate region.

6. The system as claimed in claim 1, wherein the classifying includes classifying the candidate region as one of an acute intracranial haematoma, acute subdural haematoma, acute epidural haematoma, or partial volume effect.

7. The system as claimed in claim 1, further including image acquisition apparatus which generates the non-contrasted computed tomography image data and communicates the computed tomography data to the computer.

8. A method of identifying an acute haematoma in non-contrasted computed tomography image data, the method comprising:
   extracting a candidate region suspected to be the acute haematoma, based on a first analysis of gray values of the image data including region growing and thresholding, the region growing and thresholding comprising:
   casting rays from a border of the image data,
   responsive to a ray contacting an object having a gray value greater than associated skull threshold value and with an extension greater than a preselected distance, setting a seed within the object, and
   determining a binary mask of a skull defining a skull region for extraction; and
   classifying the candidate region as a positive or negative acute haematoma, based on a second analysis of spatial features of the candidate region, wherein the spatial features include a size of the candidate region, a shape of the candidate region, and a connectedness of the candidate region to the skull.

9. The method as claimed in claim 8, wherein the computer is programmed to classify the candidate region by:
   computing a connectedness of the candidate region to the skull in accordance with a distance between the candidate region and the skull;
   computing dimensions of the candidate region; and
   classifying the candidate region in accordance with the computed connectedness and the dimensions of the candidate region.

10. The method as claim in claim 9, wherein the computer is further programmed to:
    calculate a Euclidean distance map of the brain so as to assign to each of a plurality of points of the brain, a Euclidean distance from the point to the skull;
    bin each of the plurality of points in accordance with the calculated Euclidean distance; and
    calculate a distance-based histogram including each candidate region and each bin in accordance with a mean of gray values for each candidate region and each bin, wherein classification of the candidate region is performed in accordance with the distance-based histogram.

11. The method as claimed in claim 8, further comprising:
    setting a seed within a mass center or a geometrical center of the skull region;
    determining a connected component of the seed, the connected component comprising voxels having a gray value greater than an associated brain threshold value and less than the associated skull threshold value; and
    extracting the determined connected component of the seed as the brain region.

12. The method as claimed in claim 11, further comprising:
    identifying a voxel within the brain region having a gray value greater than an associated haematoma threshold value; and
    determining a connectivity component of the identified voxel as the candidate region.

13. The method as claimed in claim 12, further comprising:
    determining a value of each of the skull threshold, the brain threshold and the haematoma threshold in accordance with a set of training images.

14. A non-transitory computer-readable storage medium storing a computer program which, when executed on a computer configures the computer to perform a method of identifying an acute haematoma in non-contrasted computed tomography image data, including:
    extracting a candidate region suspected to be the acute haematoma, based on a first analysis of gray values of the image data, the first analysis including region growing and thresholding; and
    classifying the candidate region as a positive or negative acute haematoma, based on a second analysis of spatial features of the candidate region via a distance-based histogram, wherein the spatial features include a size of the candidate region, a shape of the candidate region, and a connectedness of the candidate region to a skull.

15. A system for identifying an acute haematoma in non-contrasted computed tomography image data, the system comprising a computer programmed to:
perform a first analysis of gray values of the non-contrasted computer tomography image data, the first analysis comprising region growing and thresholding;
extract a candidate region suspected to be the acute haematoma, based on the first analysis of the gray values, the extracting comprising:
extracting a skull region by:
casting rays from a border of the image data,
responsive to a ray contacting an object having a gray value greater than an associated skull threshold value and with an extension greater than a preselected distance, setting a seed within the object, and
determining a binary mask of the skull defining the skull region for extraction;
extracting a brain region, based on the extracted skull region; and
extracting the candidate region from within the brain region;
perform a second analysis of spatial features of the candidate region, including a size of the candidate region, a shape of the candidate region, and a connectedness of the candidate region to a skull; and
classify the candidate region as a positive or negative acute haematoma, based on the analysis of the spatial features.

16. The system as claimed in claim 15, wherein the computer is further programmed to extract the brain region, based on the extracted skull region by the brain unit by:
setting a seed within a mass center or a geometrical center of the skull region;
determining a connected component of the seed, the connected component comprising voxels having a gray value than an associated brain threshold value and less than the associated skull threshold value; and
extracting the determined connected component of the seed as the brain region.

17. The system as claimed in claim 16, wherein the computer is programmed to extract the candidate region within the brain region by:
identifying a voxel within the brain region having a gray value greater than an associated haematoma threshold value; and
determining a connectivity component of the identified voxel as the candidate region.

* * * * *